United States Patent [19]

Garg

[11] Patent Number: 4,783,172

[45] Date of Patent: Nov. 8, 1988

[54] RESPIROMETER

[76] Inventor: Raj P. Garg, c/o Thapar Inst. of Engineering & Technology, Patiala, India

[21] Appl. No.: 130,425

[22] Filed: Dec. 9, 1987

Related U.S. Application Data

[63] Continuation-in-part of Ser. No. 783,632, Oct. 3, 1985, abandoned, and Ser. No. 77,165, Jul. 24, 1987.

[51] Int. Cl.$^4$ ............................................. G01N 33/18
[52] U.S. Cl. ........................ 366/142; 73/864.51; 206/527; 366/273; 383/127; 422/79
[58] Field of Search ............... 73/426, 864.51, 864.62, 73/864.91; 206/527; 366/142, 143, 273, 274; 383/127; 422/79, 225

[56] References Cited

U.S. PATENT DOCUMENTS

| | | | |
|---|---|---|---|
| 2,655,011 | 10/1953 | Ihle et al. | 366/274 |
| 3,176,517 | 4/1965 | Chelminski | 73/864.62 |
| 3,242,740 | 3/1966 | Niskin | 73/864.62 |
| 3,421,528 | 1/1969 | Gomez et al. | 366/274 |
| 3,426,745 | 2/1969 | Farr | 73/864.62 |
| 4,188,989 | 2/1980 | Andersen | 73/864.51 |
| 4,302,974 | 12/1981 | Niskin | 73/864.62 |
| 4,461,186 | 7/1984 | Brann | 73/864.62 |
| 4,568,195 | 12/1986 | Herz et al. | 366/274 |

FOREIGN PATENT DOCUMENTS 2201204 5/1973 Fed. Rep. of Germany ........ 422/79

*Primary Examiner*—Jimmy G. Foster
*Attorney, Agent, or Firm*—B. K. Niyogi

[57] ABSTRACT

A respirometer for determining oxygen demand of respiring liquid is described. The respirometer has a chamber to be filled with the liquid. The chamber includes a base plate, a cover plate, a plurality of supports extending between the base plate and the cover plate, and a side wall made of an oxygen permeable membrane. The cover plate has an opening therein which is capable of supporting a dissolved oxygen probe. The opening also acts as an inlet and outlet to the chamber. A rotor is provided in the chamber for stirring the liquid.

11 Claims, 1 Drawing Sheet

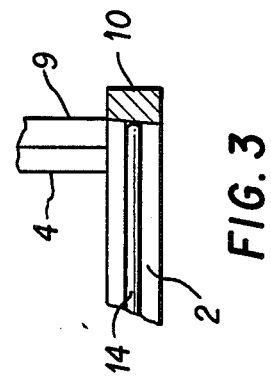
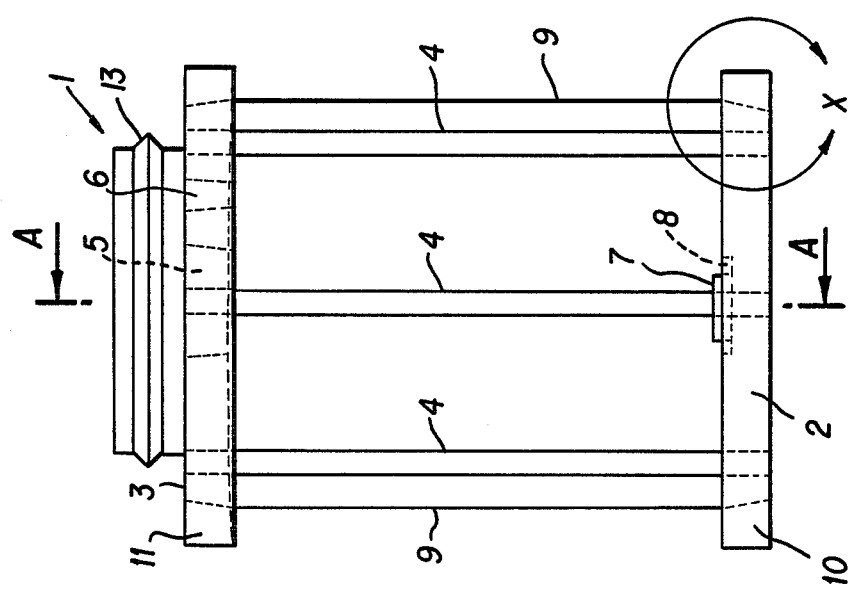
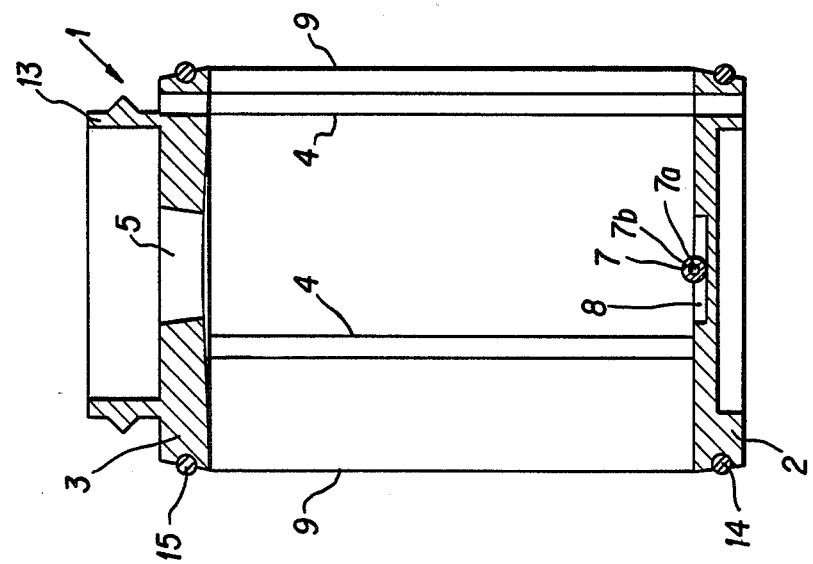

RESPIROMETER

This Application is a continuation-in-part of Ser. No. 06/783,632 filed Oct. 3, 1985, abandoned.

This application is also a co-pending continuation-in-part of application Ser. No. 077,165 filing date 7/24/87, by the same inventor, which has been allowed.

FIELD OF THE INVENTION

This invention relates to a respirometer for testing of wastewater samples to determine its BOD. The abbreviation BOD is a standardised abbreviation in the art for the Biochemical Oxygen Demand.

PRIOR ART

It is known that water contains a limited amount of dissolved oxygen. Thus, at a temperature of 20 C., 1 liter of water contains only 9.2 mg. of oxygen at saturation. Simultaneously, the consumption of oxygen is proprtional to the amount of biodegradable organic matter available in wastewater. Due to the limited amount of dissolved oxygen available in the wastewater sample, it was hitherto necessary to dilute the wastewater with specially prepared dilution water and then carry out the standard BOD test in glass bottles and referred to as BOD bottles.

Various constructions of respirometer are known in the art. One such construction envisages the use of a glass bottle, and within which the wastewater sample diluted with aerated water is introduced and stored at a fixed temperature of 20° C. for a period of 5 days. The difference between the initial and final dissolved oxygen concentration corresponds to the amount of oxygen consumed by the living organisms for stabilization of the organic matter present in said wastewater. Several distinct disadvantages are associated with such a known construction of a respirometer. One such disadvantage is that of the requirement of diluting of wastewater. Yet another disadvantage is that the results are not standardized, as it is dependant on the extent of dilution of the wastewater sample.

In order to obviate such disadvantages, yet another construction of a respirometer is known in the art. Such a respirometer comprises a reaction vessel connected to one of the arms of a manometer. The reaction vessel has a central well formed on the base for containing a solution of potassium hydroxide therein. The wastewater sample is partially filled into said vessel. The reaction vessel and, the manometer are then subjected to a mechanical agitation so as to allow absorption of oxygen. The purpose of only partially filling the vessel is to provide atmospheric air over the wastewater sample so as to allow an absorption of oxygen. Carbon dioxide evolved by the bio-chemical reaction is absorbed by solution of potassium hydroxide. It would be apparent that as oxygen is consumed by the living organisms present in the wastewater sample, the pressure within the flask reduces, which pressure is measured by the manometer. The disadvantage associated with such a known construction of a respirometer is that the instrument is elaborate and, further, means must be provided for causing an agitation of the complete instrument. Yet another disadvantage is that of leakages from the reaction vessel. A further disadvantage is that such a respirometer is not suitable for routine work. Yet another disadvantage is that variations in atmospheric pressure will cause an error in the manometric measurement.

Yet another construction of a respirometer is known in the art, which similarly comprises of a reaction vessel connected to a closed manometer and where in a likewise manner the wastewater sample is only partially filled into said vessel. A magnetic stirrer is provided at the base of the reaction vessel and, whereby, the wastewater sample is subjected to stirring. The reaction vessel has an inner and outer stopper, said inner stopper having means for storage of a solution of potassium hydroxide therein. Though, such a construction of a respirometer does obviate certain of the disadvantages associated with the respirometer described in the preceding paragraph herein, a distinct disadvantage still associated with the present construction is that it is not suitable for routine testing.

Yet another construction of a respirometer is known in the art and which avoids the use of a manometer. Such a respirometer has an electrolytic means for generating oxygen and a pressure sensitive probe. Thus, upon a drop in pressure and as sensed by the probe, oxygen is generated and released to the surrounding atmosphere so as to restore the pressure. The time period during which oxygen is generated thereby provides the measurement of oxygen consumption.

As would be apparent, the respirometers of the known art were based on the principle of difference of pressure existing within the reaction vessel during certain predetermined interval of time due to the absorption of oxygen by the waste water samples during said interval of time.

OBJECTS OF THE INVENTION

A primary object of the invention is to propose a respirometer for testing of wastewater samples to determine its BOD and, wherein, it is no longer necessary to dilute the wastewater sample.

Another object of the invention is to propose a respirometer for testing of comparatively concentrated wastewater samples to determine its BOD and, wherein, the gas phase is separated from the liquid phase and it is no longer necessary to absorb the evolved carbon dioxide in alkaline solution and, thus, natural environmental conditions are provided to the biomass in the respiring liquid.

Still another object of the invention is to propose a respirometer for testing of wastewater samples to determine its BOD and, wherein, the apparatus is suitable for routine testing.

Yet another object of the invention is to propose a respirometer for testing of wastewater samples to determine its BOD and which also provides an indication of the instantaneous rate of BOD exertion.

SUMMARY OF THE INVENTION

The respirometer of the present invention comprises a chamber adated to contain a wastewater sample therein. The chamber is formed from a membrane so as to permit oxygen to pass through it. The said chamber is formed of a base plate and a cover plate separated by a plurality of supports extending between the said base and cover plate. The cover plate has two openings, one for introduction of a dissolved oxygen probe and another for introduction of a thermometer. The cover plate has a fixed collar for storing a liquid under test such as water or wastewater sample. The cover and base plates are each slightly tapered and, preferably, in a direction opposite to each other. The base plate and cover plate is provided each with a groove for accomodation of an O-ring. Membrane, forming the walls of the chamber, is in the form of an annular membrane. The lower end of the membrane is held to the base plate with a collar complementary to it whereas the upper end of the said membrane is held to the said cover plate with a collar complementary to it. Stirring of the contained liquid in the chamber is caused by a rotor, placed in a depression in the base plate, which is rotated by a magnetic stirrer.

The chamber, of the present invention, is capable of being utilised as a respirometer for which it possesses the features of, storage and retention of a liquid such as water during the test period, reoxygenation of the contained liquid sample, completely filled and closed to the atmospheric air except through the membrane, substantially high rate of reoxygenation of the contained wastewater sample to balance a higher rate of deoxygenation occuring in a concentrated wastewater sample, repeatability of the rate and kinetic mode of reoxygenation of the chamber of the respirometer to ensure reliability of the computed values of BOD from the respirometer data.

Reference is now briefly made to the theory of the respirometer of the present invention, from which it will be apparent that the BOD of concentrated wastewater samples can be evaluated without dilution in the said respirometer.

When the respirometer is filled with the respiring liquid, processes of deoxygenation and reoxygenation take place simultaneously. The phenomenon of deoxygenation results from the consumption of dissolved oxygen on account of aerobic activity in the respiring liquid and reoxygenation replenishes, in part or full, the depleted oxygen in the respiring liquid. A higher rate of reoxygenation is thus required to balance a higher rate of deoxygenation. A high level of reoxygenation of a respirometer is thus required for the BOD determination of a concentrated wastewater sample having high concentration of oxygen consuming biodegradable organic matter. In the respirometer the quantity of oxygen exchanged between the respiring liquid and the gas is determined by estimating the amount of oxygen added to the respiring liquid due to reoxygenation and which in turn provides an estimate of the BOD of the wastewater sample.

The walls of the respirometer of the present invention are formed from a membrane which is permeable to oxygen, thus allowing reoxygenation of the contained sample by absorption of oxygen from the atmospheric air.

In the known respirometers gas and liquid phases are maintained in the chmaber to allow reoxygenation of the wastewater sample. This necessitates absorption of evolved carbon dioxide (due to aerobic activity) and determination of oxygen content of the gas phase whereby the apparatus becomes elaborate and is not suitable for routine use. Further absorption of carbon dioxide varies the rate of BOD exertion.

Such disadvantages are obviated by the membrane provided between the gas phase (atmospheric air) and the liquid phase (respiring liquid). Reoxygenation of the sample now takes place through the said membrane. In the respirometer of the present invention, gas and liquid phases are maintained separately by surrounding the wastewater sample with the said membrane and further the chamber is completely filled and any air bubbles inside it are removed initially. Removal of air bubbles is facilitated by the form of the underside of the said cover plate which slopes upward towards the centre. Absence of gas phase within the chamber of the present invention, obviates the necessity of absorption of carbon dioxide from the gas phase as in the known respirometers. Dissolved oxygen is determined in the liquid phase and, whereby, the container structure of the respirometer of the present invention, is simplified and is suitable for routine testing. Any carbon dioxide, produced due to aerobic activity gets dissolved in the liquid phase. The known membranes which are permeable to oxygen are also permeable to other gases such as carbon dioxide and nitrogen. Thus, the dissolved carbon dioxide will be in equilibrium with the carbon dioxide present in the atmospheric air (gas phase) through the same membrane. Presence of dissolved carbon dioxide, in the liquid phase, provides natural environmental conditions to the biomass in the respiring liquid, thus, enhancing the authenticity of the rate of BOD determination.

In the chamber of the respirometer of the present invention, exchange of gas takes place only through its walls which are formed from a membrane permeable to gas. The joints of dissolved oxygen probe, thermometer with the cover plate are made air tight and closed to the atmospheric air. Further by providing a fixed collar on the said cover plate, thus, storing the liquid under test, thus, preventing any leakage of gas or vapours through the said joints. Further, joints of the membrane with the base and cover plates, are made air tight. The lower end of the membrane is held tightly in between the base plate and its complementary collar. Similarly the upper end of the membrane is held tightly in between the cover plate and its complementary collar. Further, rubber O-rings are inserted in grooves in the said base and cover plates and said O-rings are kept slightly projecting outward. Thus, the respirometer is closed to the atmospheric air except through the said membrane.

Reference is now briefly made to the known film model for oxygen transfer to bring out the means providing capability to the respirometer for a substantially high rate of reoxygenation and repeatability of the rate and kinetic mode of reoxygenation of the chamber of the respirometer of the present invention.

When the contents of the respirometer are stirred, oxygen transfer in it is modelled on the "stagnant film" model. Due to mixing in the bulk liquid phase, resistance to mass transfer is confined to the membrane and a thin stagnent liquid film adjacent to the membrane. With a container structure having a particular geometric shape and also uniform rate of stirring, following assumptions are made;

(i) the thickness of the thin stagnant liquid film remains constant; and (ii) there is no hold up of dissolved oxygen in the thin stagnant liquid film.

Rate of oxygen transfer in the respirometer as per film model is given by;

$$dc/dt = K_1 a (C_s - C) \qquad (1)$$

Where
  $dc/dt$ = rate of reoxygenation of the respirometer.
  $K_1$ = Over all oxygen transfer Co-efficient.
  $a$ = ratio of the area (A) of the membrane liquid interface per unit. Volumetric capacity (V) of the respirometer i.e. $a = A/V$.
  $K_1 a = r$, and $r$ is termed as the respirometer constant.
  $C_s$ = dissolved oxygen saturation concentration in the respirometer at test temperature and pressure.

$C$ = dissolved oxygen concentration in the respirometer at test temperature and pressure at time, t.

$C_s - C = D$, and $D$ is termed as dissolved oxygen saturation deficit or saturation deficit.

Thus, referring to equation (1), the rate of reoxygenation in the respirometer, of the present invention, has been increased by maximising the respirometer constant $r(=K_1 a)$. $K_1$ is maximised by selecting a membrane material having high permeability to oxygen and also using a membrane of lesser thickness. $K_1$ is also maximised by decreasing the thickness of the thin stagnant liquid film adjacent to the membrane thus reducing overall resistance to mass transfer which is achieved by stirring the liquid in the respirometer. Further value of $a(=A/V)$ has been maximised by maximising membrane liquid interface area (A) which is achieved by stirring the liquid in the respirometer whereby renewal of membrane liquid interface occurs thus increasing the effective membrane liquid interface area (A) and thus increasing the value of, a, as in equation (1). Thus, by imparting a stirrring action to the liquid in the respirometer, its rate of reoxygenation is substantially increased. Increased rate of reoxygenation, of the respirometer of the present invention, makes it possible to study the BOD of comparatively concentrated wastewater samples.

Initially rate of reoxygenation of the respirometer is determined by fitting the experimental data to the integrated form of equation (1) from where the value of respirometer constant (r) is estimated. Reliability of the computed value of BOD from the respirometer data is ensured by reproducing and maintaining the same rate and kinetic mode of reoxgenation during the course of BOD testing as initially determined experimentally. In the respirometer of the present invention, the chamber construction as well as the expeirmental conditions ensure repeatability of $K_1$ and, a, as in equation (1) and also assumptions (i) and (ii) for equation (1) thus, ensuring repeatability of rate and kinetic mode of reoxygenation.

Values of $K_1$ and, a, as in equation (1) depend on the geometric shape of the chamber. Reproducibility of the exact geometric shape, of a chamber formed only from a thin membrane, is difficult to be achieved and maintained due to irregular random folds in the membrane when the said chamber is filled with liquid. Thus, the respirometer of the present invention is formed by the base plate, cover plate and a plurality of supports extending between the base plate and cover plate. Further, an annular membrane, having a size 1 to 2 mm more than the size of the base and cover plates, is slopped over the said plates. Further, the said annular membrane is tightly held over the base and cover plates by the respective complementary collars. Slightly projecting O-rings and the taper on the base and cover plates help in keeping the said membrane in one fixed position. The said supports extending between the said base and cover plates prevent relative movement of said base and cover plates, thereby preventing folding of the membrane. Thus, the construction of the chamber of the respirometer ensures reproducibility of the geometric shape of the chamber that is also preserved during the long course of BOD testing.

Further repeatability of $K_1$ is ensured by firstly, specifying the quality and thickness of the membrane to ensure constant value of permeability of oxygen of the membrane and secondly, by preventing changes in thickness of the thin stagnant liquid film adjacent to the membrane. This is achieved by uniform and regular movement of the said rotor which is rotated by a magnetic stirrer moving at a uniform speed. Further, the said rotor is placed in a control depression on the inner surface of the base plate which provides a guided movement to the rotor and prevents its displacement towards the edges of the said base plate. Thus, the effect of stirring, on the inside of the annular membrane, is constantly uniform thereby maintaining a certain constant thickness of thin stagnant liquid film adjacent to the membrane. Repeatability of area to volume ratio (a) as in equation (1) is ensured by the reproducibility of the exact geometric shape of the chamber and also by maintaining a constantly uniform rate of stirring to effect regular and uniform surface renewal at the membrane liquid interface. Assumptions (i) and (ii) to equation (1) are fulfilled by maintaining uniformly constant rate of stirring and also preventing any folding of the walls of the chamber during the course of BOD testing. Irregular random folding of the walls of the chamber results in localised pockets of liquid volume from where irregular random exchange of fluid takes place even if the rate of stirring is uniformly constant. Thus, the thickness of the thin stagnant liquid film adjacent to the membrane varies with time and also hold up of dissolved oxygen occurs in the said localised pockets of liquid volume and hence assumptions (i) and (ii) as in equation (1) are not fulfilled. The construction of the respirometer particularly the projecting O-rings and the taper on the base and cover plates and also the complementary collars help to maintain the fixed position of the membrane without any displacement during the course of testing thereby preventing any irregular folding of the walls of the chamber. Assumptions (i) and (ii), however, shall be fulfilled with regular and reproducible folds on the membrane, in such an instance size of membrane can be more than that of cover and base plates.

Thus, the repeatability of the rate and kinetic mode of reoxygenation of the respirometer of the present invention is ensured by the construction of the chmaber and other experimental conditions. The respirometer of the present invention was standardised experimentally and respirometer constant (r) estimated. The experimental data fitted to integrated form of equation (1) which gave a co-efficient of correlation of 0.99, thus, indicating strong association of dependent and independent variables.

From the respirometer data, the BOD of the wastewater sample is computed by the numerical integration of the basic differential equation of the 'sag curve' known in the art and which may be written as:

$$\pm \Delta D + r\bar{D} \Delta t = \Delta Y \qquad (2)$$

Where $D = C_s - C$ as in equation (1)

$r = K_1 a$ as in equation (1)

$\Delta D$ represents the change in saturation deficit due to combined effects of reoxygenation and deoxygenation in the respirometer.

$\bar{D}$ = average saturation deficit over the time interval $\Delta t$.

$\Delta Y$ = BOD of the wastewater sample over the time interval $\Delta t$.

Repeatability of rate and kinetic mode of reoxygenation (as identified from the accuracy of the value of r) enhances the reliability of the computed values of BOD from the respirometer data.

BRIEF DESCRIPTION OF THE DRAWINGS

This invention is more particularly described with reference to the following drawings, in which FIG. 1 is an elevational view of the respirometer of the present invention;

FIG. 2 is a sectional view of the respirometer of FIG.1 with Section at A—A with the complementary collars from base and cover plates removed;

FIG. 3 is an elevational view in partial section illustrating the compressed O-ring due to the complementary collar as at X of the respirometer of FIG. 1.

PREFERRED EMBODIMENT OF THE INVENTION AND DETAILED DESCRIPTION OF THE DRAWINGS

The annular membrane that may be employed to form the walls of the respirometer can be of low density polyethylene. Lower the density of polyethylene, higher will be the permeability of oxygen through it. Similarly lesser the thickness of the membrane, higher will be the rate of reoxygenation of the respirometer. In order to avoid the sagging of the walls of the respirometer during the course of testing, a thickness of 0.5 mil or more(1 mil=0.025 mm) of the membrane is preferred though not limited thereto. However membrane prepared from polymers such as polyvinyl acetate, teflon and hydrogenated polybutadiene are also suitable to form the walls of the respirometer.

The respirometer skeleton, comprising of base and cover plates and supports are to be formed from a material that is resistant to chemical and biological attack e.g. glass, lucite glass, polyethylene and stainless steel. The complementary collars may be formed from rubber, fibre plastic and polyethylene.

Referring to the drawings, the respirometer 1, of the present invention, comprises a chamber consisting of a base plate 2 and a cover plate 3 held together by means of a plurality of supports 4 disposed in a spaced relationship to each other and extending between a cover plate 3 and said base plate. Cover plate 3 has an opening 5 for introduction of a dissolved oxygen probe. Cover plate 3 has a further opening 6 for introduction of a thermometer. A rotor 7 is placed in a central depression 8 in the base plate 2. The Rotar 7 is formed from a magnetic bit 7a enclosed in teflon 7b (FIG. 2) and is rotated by moving a magnet from under the base plate 2. The movement of the magnet and that of rotor 7 is caused by a magnetic stirrer known as such in the art. The speed of magnetic stirrer is kept constant during the course of standardisation and the same speed of the stirrer is maintained during the course of BOD testing. The central depression 8 in base plae 2 retains rotor 7 therein and, thus, preventing any drift or displacement of said rotor. It has found that by providing base plate 2, rotor 7 moves on said base plate and not on the membrane as in the instance when the entire chamber is fabricated from the membrane. In such an instance and during the testing period, characteristics of the membrane will charge due to movement of the rotor on the said membrane and also occasionally the membrane may even repture, thus, spoiling the entire experimental set up. Alternatively, rotor 7 may be suspended alongwith the dissolved oxygen probe through hole 5 as is known in the art. In such an instance the size of base plate 2 may be reduced.

The chamber is formed preferably by the annular membrane 9 forming the wall surface of the respirometer. Lower end and upper end of membrane 9 are held onto the base and cover plates 2 and 3 by the complementary collars 10 and 11 respectively. Membrane 9 is formed from any suitable material permeable to oxygen so that absorption of oxygen present in atmospheric air takes place at the said membrane surface. The absorbed oxygen further diffuses in the body of the membrane 9 and is then transferred to the waste water sample contained with in the chamber of the respirometer 1. The underside surface 12, shown in FIGS. 1 and 2, of cover plate 3 is sloped upwards towards the centre to facilitate removal of entrapped air from the chamber since air bubbles rise up and are removed through the holes 5 and 6.

The chamber of respirometer 1 is closed to atmosphere except through membrane 9. This is achieved by providing sealing means at the various joints to prevent any exchange of gas or vapours from the chamber. One such sealing means comprises of collar 13, on cover plate 3, to form storage means for storing a liquid under test such as water or wastewater sample. Further sealing means are provided on the joints the lower end and upper end of membrane 9 with base plate 2 and cover plate 3 respectively. These sealing means comprise of rubber O-rings 14 and 15 provided in grooves on the circumference of base plate 2 and cover plate 3 respectively. The O-rings 14 and 15 are kept slightly projecting out from the groves by about 0.5 to 1 mm as shown in FIG. 2. The peripheral side of the base plate 2 and cover plate 3 are slightly tapered as shown in FIGS. 2 and 3. The lower end and upper end of annular membrane 9 are held tightly onto the circumference of base plate 2 and cover plate 3 by the respective complementary collars 10 and 11. The rubber O-rings 14 and 15 are compressed in the joints so formed (FIG. 3), thereby making the joints leak proof and also air tight. Thus the chamber of respirometer 1 is closed to the atmosphere except through the membrane 9. Closing the chamber of the respirometer 1 to atmospheric air (except through the membrane 9) prevents introduction of unkown quantity of oxygen through uncontrolled sources, whereby, experimental errors are grossly menimised. Tapered sides of base and cover plates 2 and 3 alongwith the O-rings 14 and 15 and the complementary collars 10 and 11 hold the lower end and upper end of annular membrane 9 tightly thus preventing its displacement during the period of testing. Alternatively the lower and upper ends of membrane 9 may be sealed to base and cover plates 2 and 3 respectively. In such an instance, the respirometer may be disposed off after use.

In operation, the respirometer is standardised by the methods known in the art. Thus the respirometer constant (r) is a known value for the respirometer for the specific thickness, quality of the membrane and under specified experimental conditions. For BOD determination of a wastewater sample, membrane 9 is changed for each test. Thus annular membrane 9 is slipped over base plate 2 and cover plate 3. The lower end of the membrane is held tightly over the base plate 2 by its complementary collar 10. Wastewater sample is filled in the chamber and any entrapped air in the chamber is removed through the holes 5 and 6. Sloping underside 12 of cover plate 3 aids in easy removal on entrapped air bubbles. Uper end of membrane 9 is tightly held in hand and the complementary collar 11 slipped over cover plate 3. Wastewater sample completely fills the chamber but partially fills the collar 3. Dissolved oxygen probe and thermometer are introduced into the openings 5 and 6 respectively. The respirometer 1 is then introduced into a constant temperature chamber and the contained liquid sample is stirred by the movements of rotor 7 caused by a magnetic stirrer. The same speed of the magnetic stirrer is maintained as it was during the course of standardisation. The dissolved oxygen probe is connected to a meter or recorder giving reading of dissolved oxygen concentration (c) at zero time, and thereafter, at various intervals of time. Knowing the dissolved oxygen concentration (c), the saturation deficit $\overline{D}$ at any particular time interval is calculated as detailed for equation (1). Thus knowing the value of respirometer constant (r) and also saturation deficit D for one interval of time $\Delta y$ the BOD or amount of oxygen consumed $\Delta y$ in the said time interval can be calculated from equation (2). Also $\Delta y/\Delta t$ determines the instantaneous rate of BOD exertion.

By selecting a respirometer of suitable r value, strong wastewaters such as 1:1 glucose glutamic acid synthetic waster of 300 mg/l can be tested without the necessity of dilution of said wastewater.

I claim:

1. A respirometer, to determine the oxygen demand of a respiring liquid, comprising a closed chamber to be completely filled with the respiring liquid, said chamber having means for providing repeatability of the rate and kinetic mode of reoxygenation of the respirometer and comprising a base plate and a cover plate, a membrane permeable to oxygen held to said base and cover plates and forming the sidewall of said chamber, a plurality of supports extending between the base plate and the cover plate so as to prevent a distortion of the chamber, opening in said cover plate for supporting a dissolved oxygen probe in an air tight relationship, said opening also being an inlet for introduction of the respiring liquid and outlet for the escape of entrapped air from within the chamber, a rotor disposed within said chamber, said membrane held to the cover and base plate in an air tight relationship.

2. A respirometer as claimed in claim 1 wherein the inner surface of the base plate has a centrally located depression for receiving a rotor and prevent a displacement during a rotation thereof.

3. A respirometer as claimed in claim 1 wherein a rotor is suspended within the chamber.

4. A respirometer as claimed in claim 1 comprising removably held collars for each of the base and cover plates so as to hold the membrane to said plates in an air tight relationship.

5. A respirometer as claimed in claim 1 wherein said membrane is sealed directly to the base and cover plates.

6. A respirometer as claimed in claim 1 wherein sealing means are provided on said cover plate and comprise a fixed collar extending upwardly from said cover plate to form storage means for a liquid.

7. A respirometer as claimed in claim 1 wherein said base and cover plates are tapered.

8. A respirometer as claimed in claim 1 comprising a groove in each of the base and cover plate for accomodating an O-ring.

9. A respirometer as claimed inclaim 8 wherein said O-rings project outwardly of the grooves.

10. A respirometer as claimed in claim 1 comprising a second opening in said cover plate for a thermometer.

11. A respirometer as claimed in claim 2 wherein said depression has diameter more than the length of the rotor.

* * * * *

Disclaimer 4,783,172.—*Raj P. Garg*, Patiala, India. RESPIROMETER. Patent dated Nov. 8, 1988. Disclaimer filed Dec. 27, 1989, by the inventor.

The term of this patent subsequent to Nov. 8, 2005, has been disclaimed.
[ *Official Gazette October 9, 1990* ]